(12) United States Patent
Dettloff et al.

(10) Patent No.: US 7,361,790 B2
(45) Date of Patent: Apr. 22, 2008

(54) PROCESS FOR PREPARING 1,3-DICHLOROACETONE

(75) Inventors: Marvin L. Dettloff, Lake Jackson, TX (US); Marty J. Null, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/588,623

(22) PCT Filed: Mar. 24, 2005

(86) PCT No.: PCT/US2005/009767

§ 371 (c)(1),
(2), (4) Date: Dec. 18, 2006

(87) PCT Pub. No.: WO2005/097722

PCT Pub. Date: Oct. 20, 2005

(65) Prior Publication Data

US 2007/0129556 A1    Jun. 7, 2007

(51) Int. Cl.
*C07C 45/63* (2006.01)
*C07D 301/02* (2006.01)
*C07D 301/24* (2006.01)

(52) U.S. Cl. .................. 568/394; 549/519; 549/520
(58) Field of Classification Search ............... None
See application file for complete search history.

(56) References Cited

U.S. PATENT DOCUMENTS

| | | | |
|---|---|---|---|
| 2,860,146 A | 11/1958 | Furman et al. |
| 3,397,240 A | 8/1968 | Kaufman et al. |
| 4,439,623 A | 3/1984 | Krieger et al. |
| 5,744,655 A | 4/1998 | Thomas et al. |
| 6,350,922 B1 | 2/2002 | Vosejpka et al. |

OTHER PUBLICATIONS

Luinstra, G.A., et al.; J. Organometallic Chem 1995, 504, 75-91, "C-H activation by aqueous platinum complexes: A mechanistic study."

*Primary Examiner*—Sikarl A. Witherspoon

(57) ABSTRACT

Epichlorohydrin is produced from acetone by (1) chlorinating acetone to form monochloroacetone; (2) disproportionating the monochloroacetone in the presence of a platinum catalyst, a strong acid and preferably a chloride source (for example, added as a salt or from hydrolysis of monochloroacetone) and some water to produce acetone and 1,3-dichloroacetone; (3) hydrogenating the 1,3-dichloroacetone in the presence of a catalyst to produce 1,3-dichlorohydrin; and (4) cyclizing the 1,3-dichlorohydrin with a base to produce epichlorohydrin.

10 Claims, No Drawings

PROCESS FOR PREPARING 1,3-DICHLOROACETONE

BACKGROUND OF THE INVENTION

The present invention relates to a process for preparing 1,3-dichloroacetone and epichlorohydrin.

It is known to prepare 1,3-dichloroacetone by the direct chlorination of acetone with chlorine. See, for example, U.S. Pat. No. 4,251,467. The process involves the use of iodine or iodine salts in greater than catalytic amounts. Iodine is very expensive ($13/kilo according to the Sep. 23, 2002 issue of The Chemical Marketing Reporter). For this reason, it is very important to recover and recycle the iodine or iodine salts in the process. The extra steps of recovering and recycling the iodine or iodine salts add significant complexity for building a commercially viable process for a commodity-type product. Another method for directly chlorinating acetone involves using methanol instead of iodine or an iodine salt. However, the major product of this process is the ketal of the chlorinated species. To get the 1,3-dichloroketone, one must hydrolyze the ketal which is not a trivial process.

It would be desirable to provide a process for preparing 1,3-dichloroacetone which would eliminate the need for using iodine and all the associated complexity of recovering and recycling it, as well as eliminate the need for hydrolyzing the ketal in the case of the latter method.

SUMMARY OF THE INVENTION

In a first aspect, the present invention is a process for preparing 1,3-dichloroacetone which comprises (1) chlorinating acetone to form monochloroacetone, and (2) disproportionating the monochloroacetone in the presence of a platinum catalyst to produce acetone and 1,3-dichloroacetone. Additionally, a strong acid and, preferably, a chloride source (for example, added as a salt or from hydrolysis of monochloroacetone) and some water may be added to help initiate the reaction.

In a second aspect, the present invention is a process for preparing epichlorohydrin which comprises (1) chlorinating acetone to form monochloroacetone;

(2) disproportionating the monochloroacetone in the presence of a platinum catalyst, optionally, a strong acid and, preferably, a chloride source (for example, added as a salt or from hydrolysis of monochloroacetone) and some water to produce acetone and 1,3-dichloroacetone;

(3) hydrogenating the 1,3-dichloroacetone in the presence of a catalyst to produce 1,3-dichlorohydrin; and (4) cyclizing the 1,3-dichlorohydrin with a base to produce epichlorohydrin.

Other aspects of the present invention will become apparent from the following detailed description and claims.

DETAILED DESCRIPTION OF THE INVENTION

The process of the present invention comprises the following steps:

(1) Chlorination

Chlorination of acetone to produce monochloroacetone (MCA) is a well known process. See, for example, U.S. Pat. No. 4,439,623 and U.S. Pat. No. 3,397,240.

(2) Disproportionation

The monochloroacetone produced in step (1) is subjected to a disproportionation reaction to produce both acetone and 1,3-dichloroacetone, in the presence of a platinum catalyst, optionally a strong acid and, preferably, a chloride source (for example, added as a salt or from hydrolysis of monochloroacetone) and some water. The products may be recovered by known methods, such as extraction or distillation.

Surprisingly, it has been found that heating monochloroacetone with a specific type of catalyst, which is a platinum catalyst, produces acetone and 1,3-dichloroacetone simultaneously, without producing any significant amount of 1,1-dichloroacetone or higher chlorinated by-products.

The platinum catalysts useful in the present invention include any platinum +2 and/or +4 catalysts. Such catalysts are described in U.S. Pat. No. 6,262,280. Examples of suitable catalysts include $PtCl_2$ and its hydrate, or an alkali metal salt (or its hydrate) of the $PtCl_4^{-2}$, $PtO_2$, chloroplatinic acid, ammonium chloroplatinate, polyamine platinum salts. It is not necessary for the catalysts to be complexed with ligands such as, for example, siloxane complexes.

Preferably, the catalysts employed in the practice of the present invention, are platinum salts. The platinum catalyst is present in a homogeneous form regardless of whether or not it is added as an insoluble salt. If some of the platinum catalyst is leached into the reaction mixture a reaction takes place. If no platinum is leached into the reaction mixture (based on Pt analyses of the liquid phase of the reaction mixture), no reaction takes place. While not wishing to be bound by theory, it is believed that this reaction is related to what goes on in the Shilov-type reaction, described in Luinstra, G. A.; Wang, L.; Stahl, S. S.; Labinger, J. A.; Bercaw, J. E. *J. Organometallic Chem* 1995, 504, 75-91, "C—H activation by aqueous platinum complexes: A mechanistic study."

(3) Hydrogenation

A key feature of the present invention is to hydrogenate the 1,3-dichloroacetone without removing a chlorine atom through the formation of HCl. Such hydrogenation process is described in U.S. Pat. Nos. 5,744,655, and 6,350,922. The hydrogenation catalysts can be homogeneous or heterogeneous with heterogeneous being most preferred. Use of a heterogeneous catalyst minimizes or eliminates the need to isolate the catalyst for continued use.

The 1,3-dichloroacetone produced in Step (2) is hydrogenated by reaction with a hydrogenating agent to produce 1,3-dichlorohydrin.

The hydrogenating agent useful in the present invention may be, for example, molecular hydrogen, an alcohol, or a combination thereof. The hydrogenating agent is preferably molecular hydrogen.

Examples of suitable alcohols useful in the present invention can be primary or secondary alcohols such as methanol, ethanol and $C_3$-$C_{10}$ primary and secondary alcohols. Preferably, the alcohol is methanol. Examples of other secondary alcohols useful in the present invention are described in U.S. Pat. No. 2,860,146.

The maximum quantity of hydrogenating agent source is not critical and is governed by practical considerations such as pressure, reactor efficiency, and safety. When the hydrogenating agent source is gaseous, then the quantity of hydrogenating agent is preferably at least enough to provide the desired pressure. However, in most cases, the reactor preferably contains no more than 1,000 moles of molecular hydrogen per mole of α-chloroketone and more preferably contains no more than 100 moles of molecular hydrogen per mole of α-chloroketone. Gaseous hydrogenating agent sources, such as molecular hydrogen, are preferably used according to known methods for mixing a gaseous reagent with a liquid reaction mixture, such as bubbling the gas through the mixture with agitation or solubilizing the hydrogen under pressure.

The hydrogenation reaction of the present invention takes place in the presence of a heterogeneous transition metal-containing catalyst.

The transition metal useful as the heterogeneous catalyst of the present invention may be one or more metals selected from any of Groups IB, IIB or IIIA-VIIIA on the periodic table of elements, as currently adopted by the International Union of Pure and Applied Chemistry (IUPAC). The catalyst metal is preferably selected from Group VIIIA of the IUPAC periodic table, including for example, iron, cobalt, nickel, ruthenium, rhodium, palladium, osmium, iridium, platinum and mixtures thereof. The catalyst metal is most preferably platinum.

The temperature of the reaction is not critical, provided that all of the reagents, aside from the hydrogen, remain liquid and in contact with each other. However, low temperatures require longer reaction times and lead to increased levels of impurities. The reaction temperature is preferably at least −10° C., more preferably at least 20° C. and most preferably at least 50° C. The reaction temperature is preferably less than 250° C., more preferably no more than 100° C. and, most preferably no more than 85° C.

The reaction pressure is not critical as long as there is sufficient hydrogen to run the reaction in the reaction mixture. The pressure is preferably at least 14 psi (97 kPa, 1 atmosphere) and more preferably at least 50 psi (340 kPa, 3.4 atmospheres). The pressure is preferably no more than 3,000 psi (21 MPa, 220 atmospheres). Higher pressures lead to shorter reaction times.

(4) Ring-Forming or Cyclizing Step

The 1,3-dichlorohydrin produced in step (3) is cyclized to produce epichlorohydrin by contacting it with a strong base, such as an aqueous alkali metal hydroxide, including, for example, sodium hydroxide. This step is well known in the art of manufacturing epihalohydrin. See, for example, U.S. Pat. No. 2,860,146.

The process of the present invention can be represented by the following general equation:

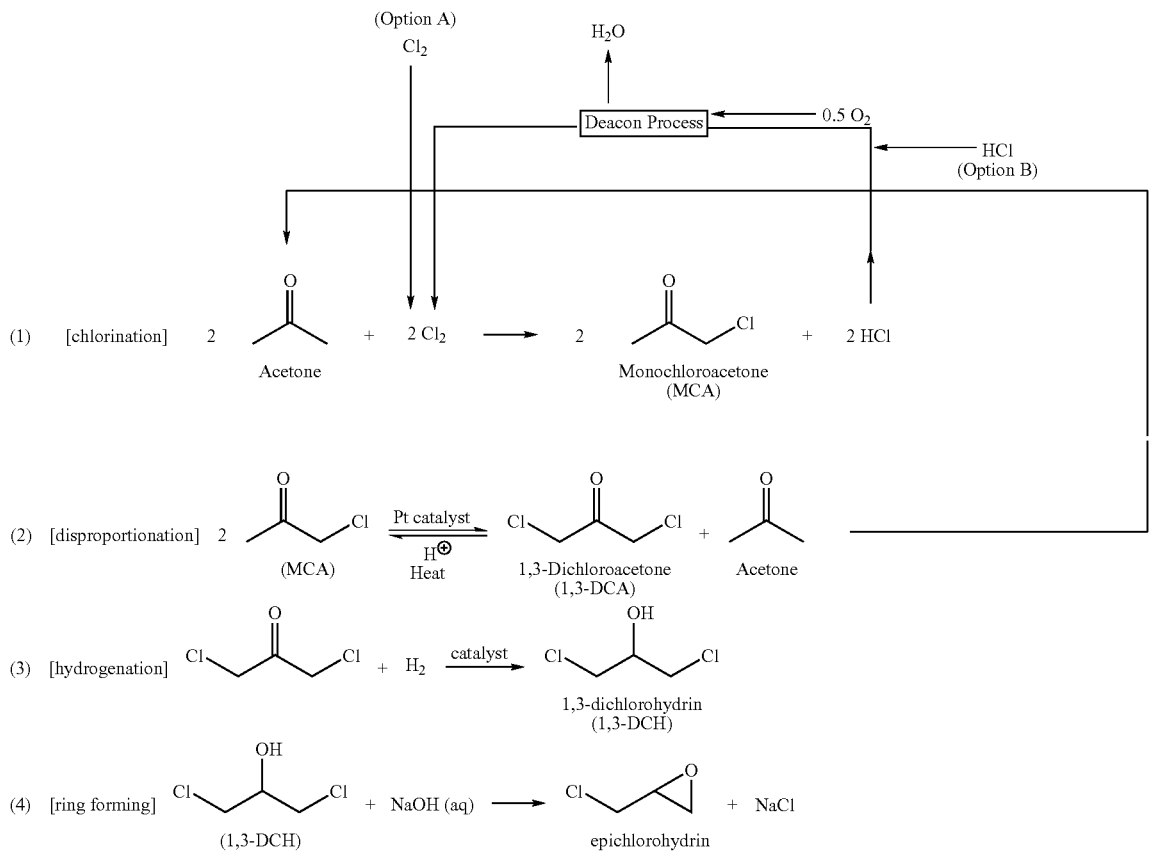

The Deacon Process comprises producing chlorine by direct oxidation of gaseous HCl with $O_2$ in the presence of a $CuCl_2$ catalyst. This process is described by the overall chemical equation:

$$HCl(g) + \tfrac{1}{4}O_2(g) \rightarrow \tfrac{1}{2}H_2O(g) + \tfrac{1}{2}Cl_2(g). \tag{1}$$

Reaction (1) in the presence of a $CuCl_2$ catalyst is a fast overall exothermic process, which is expected to reach equilibrium under normal industrial operating conditions of 700° K. to 750° K.

The following working examples are given to illustrate the invention and should not be construed as limiting its scope. Unless otherwise indicated, all parts and percentages are by weight.

EXAMPLES 1 TO 4

GC Conditions
GC: HP 5890 II with FID and 6890 auto-injectors (Front detector)
Column: Rtx-35, Restek Corp., Cat # 10453, ser# 441628
Column type: 35 percent diphenyl-65 percent dimethyl polysiloxane
Column dimensions: 30 m×0.25 mm×1.0 um
Head pressure: 25 psi
Split vent flow: 50 mL/min
Purge gas flow: 4 mL/min
Air flow: ~300 mL/min
Hydrogen flow: 30 mL/min
Make-up flow: 30 mL/min (column flow ~4 mL/min)
Temperature ramp: 55° C. for 4 min hold, +15° C./min to 250° C. for 10 min.
Run time: 27 minutes
Injector volume: 0.5 uL (5 uL syringe)
Injector temp: 200° C.
Detector temp: 290° C.
Solvent washes: A=acetonitrile, B=50/50 acetonitrile/water
Integrator: HP ChemStation The disproportionation reactor was a 4-dram vial equipped with a magnetic stir bar. Monochloroacetone was added to the reactor which contains water, a catalyst as shown in Table I and a strong acid and preferably a chloride salt. The relative amounts of the materials are shown in Tables I-IV. The mixture was stirred and then heated at 95 to 100° C. for 17 hours. The product was cooled to room temperature. Ten drops of the filtrate was diluted to 1 mL with acetonitrile, then filtered through a disposable syringe filter and analyzed by gas chromatography. The amounts of products produced are reported by GC area percentages as shown in Tables I to IV (EXAMPLES 1 to 4, respectively).

TABLE I

Results for MCA with Different Non-supported Catalysts
(NOTE: All samples contain MCA and catalyst. Water added to all reaction mixtures.)

| Catalyst | Moles cat./Moles MCA | Moles Cl/Moles MCA | Moles H20/Moles MCA | Area Percent MCA Remaining | Area Percent 1,3-DCA | Area Percent 1,1,3-TCA | Area Percent 1,1-DCA | Area Percent Acetone |
|---|---|---|---|---|---|---|---|---|
| HHCP (aq)* | 0.0021 | 0.013 | 0.57 | 81 | 6.4 | 0.01 | 2.36 | 8 |
| $PtCl_2$ | 0.0025 | 0.0051 | 0.17 | 61 | 11.3 | 0.06 | 2.22 | 10.1 |
| $PtO_2$ | 0.0025 | 0 | 0.15 | 65 | 11.3 | 0.05 | 2.24 | 9.3 |
| $PtCl_2$/$H_2Pt(OH)_6$** | 0.0026 | 0.0046 | 0.06 | 59 | 10.0 | 0.05 | 2.34 | 7.96 |
| Pt powder | 0.0030 | 0.0093 | 0.15 | 94 | 0.27 | 0.00 | 2.03 | 1.71 |
| $CoCl_2$ | 0.0027 | 0.0054 | 0.15 | 94 | 0.27 | 0.01 | 2.06 | 1.77 |
| $CuCl_2$ | 0.0026 | 0.0051 | 0.16 | 92 | 0.28 | 0.00 | 2.05 | 1.77 |
| $CuCl_2$ (repeat) | 0.0026 | 0.0053 | 0.14 | 95 | 0.28 | 0.00 | 2.05 | 1.06 |
| CuCl | 0.0027 | 0.0055 | 0.16 | 94 | 0.28 | 0.00 | 1.97 | 1.69 |
| $FeCl_3$ | 0.0024 | 0.0047 | 0.16 | 94 | 0.27 | 0.01 | 2.03 | 1.99 |
| $HgCl_2$ | 0.0024 | 0.0047 | 0.15 | 94 | 0.27 | 0.01 | 2.03 | 1.94 |
| $IrCl_3$ | 0.0024 | 0.0047 | 0.14 | 95 | 0.26 | 0.00 | 2.01 | 0.50 |
| $IrCl_4$ | 0.0025 | 0.0050 | 0.14 | 94 | 0.26 | 0.01 | 2.05 | 1.76 |
| $PdCl_2$ | 0.0024 | 0.0047 | 0.17 | 94 | 0.27 | 0.01 | 2.03 | 1.93 |
| $RuCl_2$ | 0.0023 | 0.0047 | 0.14 | 95 | 0.26 | 0.00 | 1.85 | 1.73 |
| $RhCl_2$ | 0.0022 | 0.0045 | 0.17 | 94 | 0.27 | 0.02 | 2.03 | 1.67 |
| TlCl3 | 0.0029 | 0.0057 | 0.15 | 94 | 0.27 | 0.01 | 2.03 | 1.83 |
| TlCl | 0.0026 | 0.0052 | 0.16 | 95 | 0.26 | 0.00 | 2.02 | 0.72 |
| $ZrCl_4$ | 0.0030 | 0.0061 | 0.13 | 71 | 0.35 | 0 | 3.09 | 2.62 |
| MCA only | NA | NA | NA | 95 | 0.17 | 0.00 | 2.28 | 0 |

*HHCP = hydrogen hexachloroplatinate (IV), 8 wt percent solution in water. Formula weight $H_2PtCl_6$ = 409.82.
**The PtCl2 contributed ~46 percent of the moles of Pt.
A source of a strong acid is preferred at the beginning of the reaction. It helps to accelerate the reaction.

The data in Table I show that only the Pt(+2) and Pt(+4) catalysts produced significant amounts of 1,3-dichloroacetone without producing any significant amounts of 1,1-dichloroacetone or higher chlorinated by-products.

TABLE II

Results for MCA with $PtO_2$ (with and without HCl) vs Time
(NOTE: All samples contain MCA (2 g). 5 wt percent HCl was used with $PtO_2$ and 11 wt percent HCl was used with Pt/carbon)

|  | Time (hours) | Moles Pt/ Moles MCA | Moles Cl/ Moles MCA | Moles H20/ Moles MCA | Area Percent MCA Remaining | Area Percent 1,3-DCA | Area Percent 1,1,3-TCA | Area Percent 1,1-DCA |
|---|---|---|---|---|---|---|---|---|
| $PtO_2$ (no HCl) | 6.5 | 0.0027 | 0 | 0.15 | 92 | 1.0 | 0.01 | 2.05 |
| $PtO_2$ (with HCl) | 6.5 | 0.0027 | 0.0076 | 0.29 | 79 | 7.8 | 0.02 | 2.07 |
| PtO2 (no HCl) | ~22.5 | — | 0 | — | 60 | 11.2 | 0.05 | 2.31 |
| PtO2 (with HCl) | ~22.5 | — | 0.0076 | — | 65 | 11.3 | 0.05 | 2.24 |
| MCA only | NA | NA | NA | NA | 95 | 0.17 | 0 | 2.28 |

The data in Table II indicate that adding HCl to the reaction mixture in the presence of a platinum catalyst early in the reaction (6.5 hours after start of reaction) helps get the reaction started sooner.

TABLE III

Results for MCA with Different Acids
(NOTE: All samples contain MCA (2 g), 5 wt percent Pt on carbon (0.2 g), acid and water)

| Acid | Moles Pt/ Moles MCA | Moles Cl/ Moles MCA | Moles H20/ Moles MCA | Area Percent MCA Remaining | Area Percent 1,3-DCA | Area Percent 1,1,3-TCA | Area Percent 1,1-DCA |
|---|---|---|---|---|---|---|---|
| HCl | 0.0023 | 0.029 | 0.468 | 73 | 10 | 0.04 | 2.32 |
| $H_2SO_4$ | 0.0026 | 0 | 0.549 | 90 | 2 | 0.02 | 1.99 |
| p-TSA hydrate* | 0.0025 | 0 | 0.457 | 80 | 3 | 0.01 | 2.37 |
| MCA only | NA | NA | NA | 95 | 0.17 | 0 | 2.28 |

*p-TSA = para-toluenesulfonic acid dihydrate

The data in Table III indicate that HCl performs better than the other strong acids for running the disproportionation reaction.

TABLE IV

Results for MCA with 5 wt percent Pt on carbon catalyst and LiCl
(NOTE: All samples contain MCA (2 g) and 5 wt percent Pt on carbon (0.2 g))

|  | Moles p-TSA*/ Moles MCA | Moles Cl/ Moles MCA | Moles H20/ Moles MCA | Area Percent MCA Remaining | Area Percent 1,3-DCA | Area Percent 1,1,3-TCA | Area Percent 1,1-DCA |
|---|---|---|---|---|---|---|---|
| MCA only | NA | NA | NA | 95 | 0.17 | 0.00 | 2.28 |
| LiCl (dry) | 0 | 0.228 | 0 | 85 | 5 | 0.03 | 2.15 |
| LiCl + Water | 0 | 0.156 | 0.450 | 84 | 6 | 0.02 | 2.11 |
| LiCl + p-TSA | 0.051 | 0.255 | 0.102 | 63 | 15 | 0.11 | 2.28 |
| p-TSA only | 0.052 | 0 | 0.104 | 63 | 0.22 | 0.02 | 3.18 |

*p-TSA = para-toluenesulfonic acid dihydrate

The data in Table IV indicate that a chloride salt helps generate the disproportionation reaction.

What is claimed is:

1. A process for producing 1,3-dichloroacetone which comprises (1) chlorinating acetone to form monochloroacetone, and
   (2) disproportionating the monochloroacetone in the presence of a platinum catalyst, a chloride source, water and, optionally, a strong acid to produce acetone and 1,3-dichloroacetone.

2. The process of claim 1 wherein the platinum catalyst is selected from the group consisting of $PtCl_4^{-2}$, $PtO_2$, chloroplatinic acid, ammonium chloroplatinate, and polyamine platinum salts.

3. The process of claim 1 wherein the strong acid is hydrochloric acid.

4. A process for producing epichlorohydrin which comprises (1) chlorinating acetone to form monochloroacetone; (2) disproportionating the monochloroacetone in the presence of a platinum catalyst, a chloride source, water and, optionally, a strong acid to produce acetone and 1,3-dichloroacetone; (3) hydrogenating the 1,3-dichloroacetone in the presence of a catalyst to produce 1,3-dichlorohydrin; and (4) cyclizing the 1,3-dichlorohydrin with a base to produce epichlorohydrin.

5. The process of claim 4 wherein the hydrogenating agent is molecular hydrogen, an alcohol, or a combination thereof.

6. The process of claim 4 wherein the catalyst is a heterogeneous transition metal-containing catalyst.

7. The process of claim 4 wherein the hydrogenating agent is molecular hydrogen.

8. The process of claim 4 wherein the 1,3-dichloroacetone produced in step (2) is hydrogenated without removing a chlorine atom through the formation of HCl.

9. The process of claim 4 wherein the 1,3-dichlorohydrin produced in step (3) is cyclized to produce epichlorohydrin by contacting it with a strong base.

10. The process of claim 4 wherein the strong base is an aqueous alkali metal hydroxide.

* * * * *